US008241857B2

(12) United States Patent
Akamatsu et al.

(10) Patent No.: US 8,241,857 B2
(45) Date of Patent: Aug. 14, 2012

(54) METHOD FOR DETECTION OF PNEUMOCOCCUS

(75) Inventors: Suguru Akamatsu, Osaka (JP); Yoko Saijo, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/935,704

(22) PCT Filed: Mar. 31, 2009

(86) PCT No.: PCT/JP2009/001474
§ 371 (c)(1),
(2), (4) Date: Sep. 30, 2010

(87) PCT Pub. No.: WO2009/122714
PCT Pub. Date: Oct. 8, 2009

(65) Prior Publication Data
US 2011/0020848 A1    Jan. 27, 2011

(30) Foreign Application Priority Data
Mar. 31, 2008    (JP) .................................. 2008-089619

(51) Int. Cl.
*G01N 33/531* (2006.01)
(52) U.S. Cl. ....... 435/7.1; 435/7.32; 435/7.92; 435/975; 530/387.1; 530/388.1; 424/130.1; 424/164.1; 424/244.1; 424/165.1; 424/141.1; 424/150.1
(58) Field of Classification Search .................... None
See application file for complete search history.

(56) References Cited

U.S. PATENT DOCUMENTS
6,824,997 B1    11/2004    Moore et al.

FOREIGN PATENT DOCUMENTS
WO    WO 02/45742    6/2002

OTHER PUBLICATIONS

Uffe B. Skov Sorensen, "Pneumococcal Polysaccharide Antigens: Capsules and C-polysaccharide", An Immunochemical Study, Vo. 42, No. 1, Feb. 1995, pp. 47-53.
Hans Holmberg, et al., "Detection of C Polysaccharide in *Streptococcus* Pneumonia in the Sputa of *Pneumoniae* Patients by an Enzyme-Linked Immunosorbernt Assay", Journal of Clinical Microbiology, vol. 22, No. 1, Jul. 1985, pp. 111-115.
A.M. Sjögren, et al. "Etiologic Diagnosis of Pneumonia by Antigen Deteciton: Crossreactions Between Pneumococcal C-Polysaccharide and Oral Microorganisms", Diagn. Microbiol. Infect Dis, (6), 1987, pp. 239-248.
J. Donald Coonrod, et al. "Detection of Type-Specific Pneumococcal Antigens by Counterimmunoelectrophoresis. II. Etiologic Diagnosis of Pneumococcal Pneumonia", Etiologic Diagnosis of Pneumococcal Pneumonia, vol. 81, No. 5, 1973, pp. 778-786.

Ralph D. Feigin, et al., Countercurrent Immunoelectrophoresis of urine as well as of CSF and Blood for Diagnosis of Bacterial Meningitis, Brief Clinical and Laboratory Observations, vol. 89, No. 5, 1976, pp. 773-775.
Gloria W. Ajello, et al., "Commercial Latex Agglutination Tests for Detection of *Haemophilus influenzae* Type b and *Streptococcus pneumoniae*", Journal of Clinical. Microbiology, vol. 25, No. 8, Aug. 1987, pp. 1388-1391.
Terri L. Ballard, et al., "Comparison of Three Latex Agglutination Kits and Counterimmunoelectrophoresis for the detection of Bacterial Antigens in a Pediatric Population", Pediatr. Infect. Dis. J. vol. 6, No. 7, 1987, pp. 630-634.
Takao Kobayashi, et al, "Evaluation of *Streptococcus pneumoniae*-urinary Antigen Detection Kit in Patient with Community Acquired Pneumonia", The Journal of the Japanese Association for Infectious Diseases, vol. 76, No. 12, 2002, pp. 995-1002 (with English abstract).
Kazuhiro Tateda, "Urinary Antigen Detection Test by an Immunochromatographic Test for Diagnosis of Pneumococcal Pneumonia", Modern Media, vol. 51, No. 6, 2005, 7 pages (with English translation).
Akiyoshi Nariai, et al., "Evaluation of *Streptococcus pneumoniae* Urinary Antigen Test in Healthy Children with Nasopharyngeal Pneumococcal Carriage", The Journal of the Japanese Association for Infectious Diseases, vol. 78, No. 1, 2004, pp. 18-21, (with English abstract).
Dah-Hsing Tzeng, et al., "Diagnostic Value of the Binax NOW Assay for Identifying a Pneumococcal Etiology in Patients with Respiratory Tract Infection", J. Microbiol. Immunol. Infect., 39, 2006, pp. 39-44.
Koji Azumagawa, et a., "Evaluation of Utility of a Nasally Secreted *Streptococcus pneumoniae*—Antigen Detection test by Immunochromatography in Patients with Childhood Pneumonia", Japanese Journal of Pediatrics, vol. 58, No. 1, 2005, 139-143 (with English translation).
Kristin Stuertz, et al., "Enzyme Immunoassay Detecting Teichoic and Lipoteichoic Acids Versus Cerebrospinal Fluid Culture and Latex Agglutination for Diagnosis of *Streptococcus pneumoniae* Meningitis", Journal of Clinical Microbiology, vol. 36, No. 8, Aug. 1998, pp. 2346-2348.
Jan Kolberg, et al., "Detection of the Phosphorylcholine epitope in *Streptococci*, Haemophilus and Pathogenic Neisseriae by Immunoblotting", Microbial Pathogenesis, vol. 22, 1997, pp. 321-329.
Herman Mattie, et al., "Pharmacodynamics of Antibiotics with Respect to Bacterial Killing of and Release of Lipoteichoic Acid by *Streptococcus pneumoniae*", Journal of Antimicrobial Chemotherapy, vol. 56, 2005, pp. 154-159.

(Continued)

*Primary Examiner* — Jennifer Graser
(74) *Attorney, Agent, or Firm* — Oblon, Spivak, McClelland, Maier & Neustadt, L.L.P.

(57) ABSTRACT

To provide an immunological detection method which can detect or quantify a pneumococcal antigen in a sample derived from a living body conveniently, rapidly, and with high sensitivity, and an antibody for use in the method. The present invention provides an antibody which specifically recognizes a pneumococcal F-antigen; a method for detecting or quantitating a pneumococcal antigen, characterized in that the method detects or quantitates a pneumococcal F-antigen in a sample derived from a living body through immunological assay employing the antibody; and a kit for detecting a pneumococcal antigen, the kit containing the antibody.

11 Claims, 7 Drawing Sheets

OTHER PUBLICATIONS

International Search Report issued May 12, 2009, in PCT/JP2009/001474.
Extended European Search Report issued Mar. 30, 2011, in European Patent Application No. 09726757.9.
W. Douglas Waltman II, et al., "Cross-Reactive Monoclonal Antibodies for Diagnosis of Pneumococcal Meningitis", Journal of Clinical Microbiology, vol. 26, No. 9, XP-002628071, Sep. 1988, pp. 1635-1640.
K. Stuertz, et al., "Differential Release of Lipoteichoic and Teichoic Acids from *Streptococcus pneumoniae* as a Result of Exposure to β-Lactam Antibiotics, Rifamycins, Trovafloxacin, and Quinupristin-Dalfopristin", Antimicrobial Agents and Chemotheraphy, vol. 42, No. 2, Feb. 1998, pp. 277-281.
Larry S. McDaniel, et al., "A protective monoclonal antibody that reacts with a novel antigen of pneumococcal teichoic acid", Microbial Pathogenesis, vol. 3, No. 4, XP-023312986, Oct. 1, 1987, pp. 249-260.
Maria A. Marcos, et al., "New rapid antigen test for diagnosis of pneumococcal Meningitis", The Lancet, vol. 357, No. 9267, XP-004806121, May 12, 2001, pp. 1499-1500.

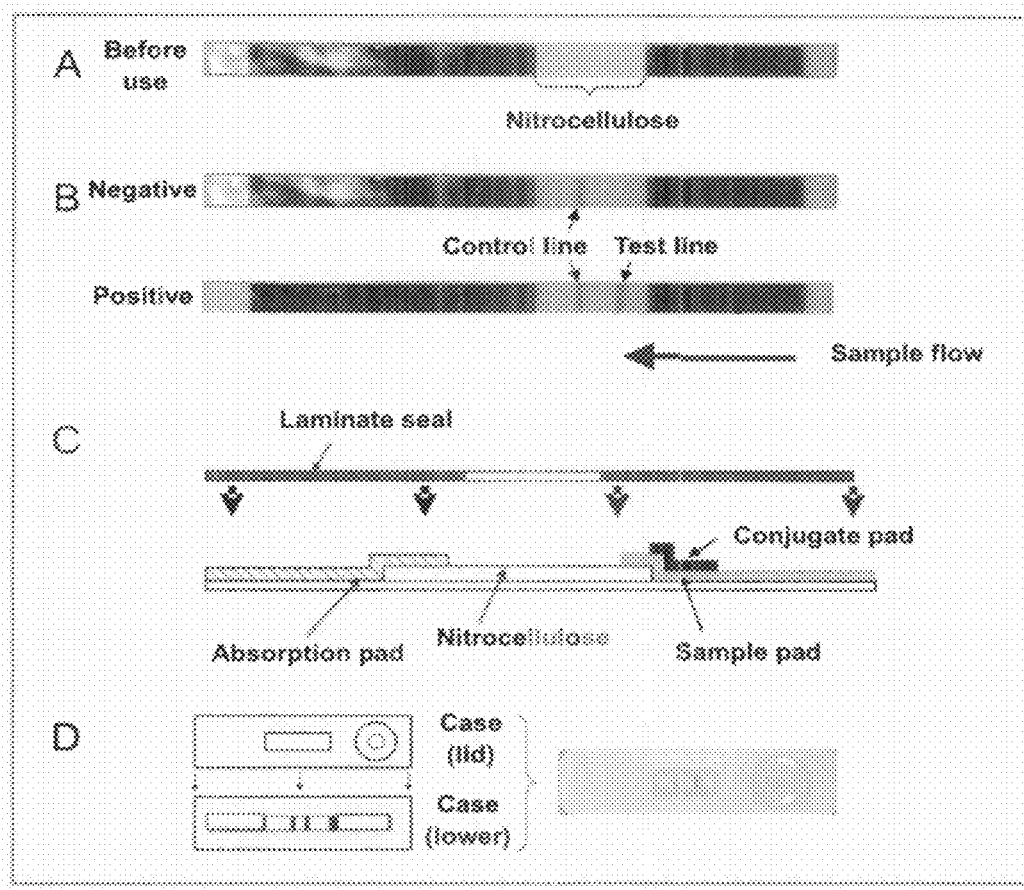

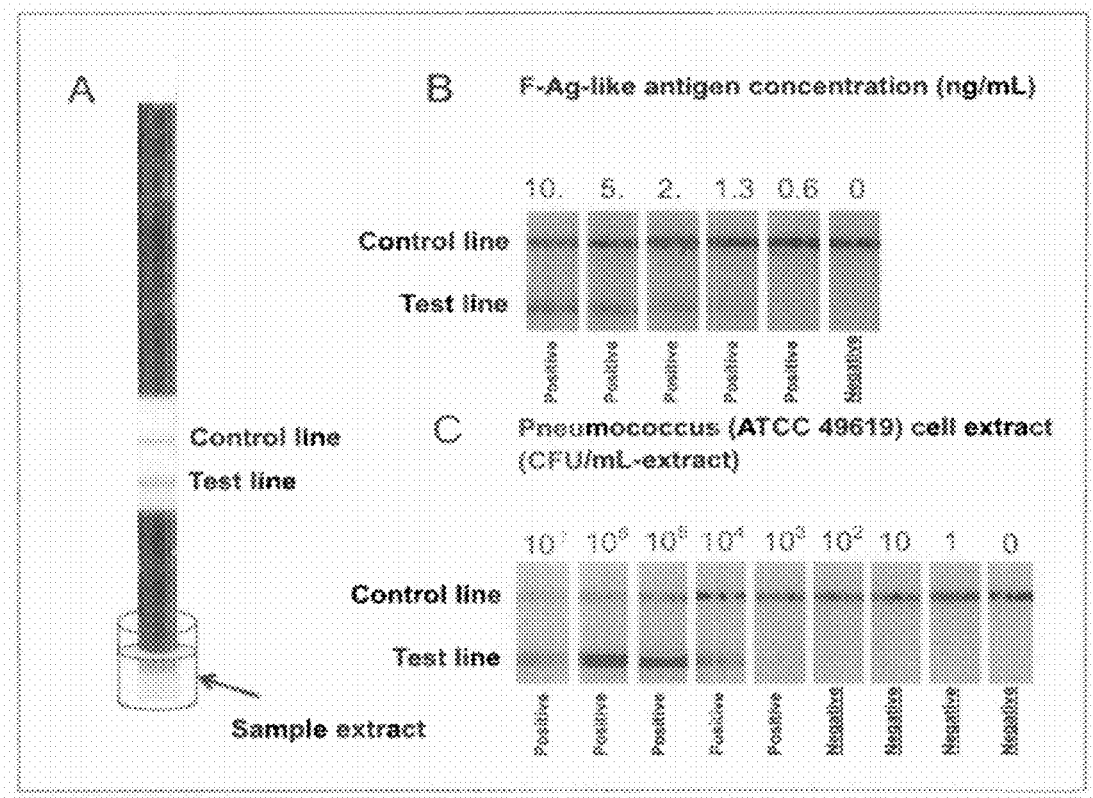

METHOD FOR DETECTION OF PNEUMOCOCCUS

TECHNICAL FIELD

The present invention relates to an immunological assay method for detecting or quantifying a pneumococcal antigen in a sample derived from a living body.

BACKGROUND ART

Pneumococcus (*Streptococcus pneumoniae*) is one of the most frequently found pathogenic bacteria for community-acquired pneumonia and lower respiratory tract infections, showing high morbidity and mortality in the world, including Japan. Since infections caused by pneumococcus occur at high incidence rate and tend to become severe, selection of an appropriate antimicrobial drug is a key to the treatment at the start thereof. According to the principle of treatment of infections, determination of the pathogenic bacterium at as early a stage as possible is also important, since an appropriate remedy can be employed at an early stage, leading to improvement in prognosis, reduction in medical cost, and prevention of generation of resistant bacteria. Under such circumstances, there is demand for a diagnostic drug for rapidly detecting a pneumococcus-derived antigen at an early stage of infection.

Sorensen et al. have reported the structure of pneumococcus in detail (Non-Patent Document 1). The outermost surface of the cell is formed of a capsular, and a polysaccharide antigen, called capsular polysaccharide, is ligated to the capsular. Hitherto, some tens or more of serum types are known in accordance with various structures of capsular polysaccharides. Meanwhile, the pneumococcus has a cell wall inside the capsular and a plasma membrane inside the cell wall. C-polysaccharide (C-ps) is ligated to the cell wall, and teichoic acid or lipoteichoic acid, called an "F-antigen," is ligated to the plasma membrane. C-ps is known to be a common antigen maintained in all capsular types of pneumococcus species, and the polysaccharide moiety of the F-antigen is known to have the same saccharide sequence as that of C-ps.

Hitherto, there have been known methods for detecting a pneumococcal antigen through employment of immunoassay. Examples of such methods include a detection method in which a C-ps antigen in a sputum sample is detected through ELISA employing an anti-C-ps antibody (Non-Patent Documents 2, 3), and a detection method in which a capsular polysaccharide (antigen) in a serum sample or a urine sample is detected through immuno-electrophoresis (Non-Patent Documents 4, 5).

Conventionally, there have been used pneumococcus detection kits based on the latex agglutination method, which kits detect a pneumococcal antigen in a cerebrospinal fluid sample, a serum sample, or a urine sample. The principle of the kits is thought to be based on detection of a polysaccharide moiety of capsular polysaccharide or the like (Non-Patent Documents 6, 7). At present, however, substantially no kit based on the latex agglutination method is employed due to cumbersome operation and unsatisfactory sensitivity.

Currently, simpler detection means are employed. One of such means is a speedy detection kit for an antigen in urine (Binax NOW (registered trademark), *Streptococcus pneumoniae* urinary antigen test, product of Binax Inc.). In this kit, C-ps present in a urine sample is detected through immunochromatography (Patent Document 1). This method is non-invasive, since an antigen in a urine sample is detected. The time required for the detection is as short as about 15 minutes (Non-Patent Document 8). However, this method (detection of antigen in urine) has a drawback in that a false positive result may be obtained due to continuous excretion of pneumococcus for a long period of time after termination of the relevant therapy (Non-Patent Document 9). In addition, difficulty is encountered in collecting urine from infants, and a false positive result may be obtained from the influence of an indigenous pneumococcus (Non-Patent Document 10). The kit is thought to provide slightly low sensitivity (Non-Patent Document 11).

A more recently developed kit; i.e., a pneumococcal antigen detection kit (Non-Patent Document 12), rapidly detects a pneumococcal antigen (C-ps) in a sputum sample, a swab of the nasal cavity, a swab of the epipharynx, a middle ear fluid sample, or an otorrhea fluid, through immunochromatography employing an anti-C-ps-polyclonal antibody (rabbit). As compared with the aforementioned diagnosis kit for an antigen in urine, the recently developed kit attains high sensitivity, and allows a clinical specimen (e.g., swab) to be analyzed without performing a concentration operation in advance. Furthermore, the detection of the antigen from a middle ear fluid sample, which was previously difficult, can be realized. Unlike a urine specimen, a sample can be easily obtained from infants. However, when certain samples such as those derived from the middle ears and the paranasal sinuses are analyzed by the kit, the sensitivity is still unsatisfactory. Thus, there is demand for such an antigen detection method attaining higher sensitivity.

As described above, there have already been reported pneumococcal antigen detection kits which detect capsular antigens or C-ps. Of these two type of kits, kits that detect capsular antigens require provision of various antibodies corresponding to various capsular antigens, and therefore, such kits are not useful as a simple assay tool. Regarding the second type; i.e., kits detecting C-ps, further enhancement in sensitivity is required in consideration of the performance test results of the aforementioned existing kits.

In contrast, the F-antigen has not been employed in routine clinical tests. Although there have been disclosed some immunological detection methods in which an anti-F-antigen antibody is employed, to detect a bacterium containing a pneumococcal antigen (Non-Patent Documents 13 to 15), in these methods, cross-reaction may occur between different bacteria, and a false negative result may be obtained, causing problematic assay accuracy.

RELATED ART DOCUMENTS

Patent Document 1: U.S. Pat. No. 6,824,997
Non-Patent Document 1: Sorensen, Danish Medical Bulletin 42: 47-53 (1995)
Non-Patent Document 2: Holmberg et al., J. Clin. Microbiol. 22: 111-115 (1985)
Non-Patent Document 3: Sjogren et al., Diagn. Microbiol. Infect. Dis. 6: 239-248 (1987)
Non-Patent Document 4: Coonrod et al., J. Lab. Clin. Med. 81: 778-786 (1973)
Non-Patent Document 5: Feigin et al., The Journal of Pediatrics 89: 773-775 (1976)
Non-Patent Document 6: Ajello et al., J. Clin. Microbiol. 25: 1388-1391 (1987)
Non-Patent Document 7: Ballard et al., Pediatr. Infect. Dis. J. 6: 630-634 (1987)
Non-Patent Document 8: Takao KOBAYASHI et al., The Journal of the Japanese Association for Infectious Diseases, Vol. 76, No. 12: 995-1002 (2002)
Non-Patent Document 9: Kazuhiro TATEDA, Modern Media, Vol. 51, No. 6: 129-132 (2005)

Non-Patent Document 10: Akiyoshi NARIAI et al., The Journal of the Japanese Association for Infectious Diseases, Vol. 78, No. 1: 18-21 (2004)
Non-Patent Document 11: Tzeng et al., J. Microbiol. Immunol. Infect. 39: 39-44 (2006)
Non-Patent Document 12: Koji AZUMAGAWA et al., Journal of Clinical Pediatrics, 58(1): 139-143 (2005)
Non-Patent Document 13: Kolberg et al., Microbial Pathogenesis 22: 321-329 (1997)
Non-Patent Document 14: Stuertz et al., J. Clin. Microbiol. 36: 2346-2348 (1998)
Non-Patent Document 15: Mattie et al., J. Antimicrob. Chemother. 56: 154-159 (2005)

DISCLOSURE OF THE INVENTION

Problems to be Solved by the Invention

An object of the present invention is to provide an immunological detection method which can detect or quantify a pneumococcal antigen in a sample derived from a living body conveniently, rapidly, and with high sensitivity. Another object of the invention is to provide an antibody for use in the method.

Means for Solving the Problems

The present inventors have conducted extensive studies on the method which can detect or quantify a pneumococcal antigen with higher sensitivity, and have produced an antibody that specifically recognizes, among pneumococcus polysaccharide antigens, a pneumococcal F-antigen, which has not been substantially used for detecting a pneumococcal antigen. As a result, the inventors have found that, through the immunological assay method employing the produced antibody, a pneumococcal antigen in a sample derived from a living body can be assayed rapidly in a simple manner with higher sensitivity, as compared with conventional methods. The present invention has been accomplished on the basis of this finding.

Accordingly, the present invention provides an antibody which specifically recognizes a pneumococcal F-antigen. The present invention also provides a method for detecting or quantitating a pneumococcal antigen, characterized in that the method detects or quantitates a pneumococcal F-antigen in a sample derived from a living body through immunological assay employing the antibody. The present invention also provides a kit for detecting a pneumococcal antigen, the kit containing the antibody.

Effects of the Invention

The present invention provides a novel antibody which specifically recognizes a pneumococcal F-antigen, and a method for detecting or quantitating a pneumococcal antigen rapidly in a simple manner, characterized in that the method detects or quantitates a pneumococcal F-antigen in a sample derived from a living body through immunological assay employing the antibody. According to the method of the present invention, a pneumococcal antigen can be detected or quantitated with higher sensitivity as compared with conventional methods. Thus, reliable assay results can be obtained, without performing a sample concentration procedure, from urine, sputum, or swab of the nasal cavity or the epipharynx, as well as from samples derived from the middle ears or the paranasal sinuses, which samples are required to be detected with higher sensitivity as compared with conventionally obtained sensitivities. In addition, the method of the present invention is clinically useful, since the method can enhance accuracy and reduce time required for identifying the causal bacterium for diseases such as meningitis, otitis media, and sepsis, caused by pneumococcus.

BRIEF DESCRIPTION OF THE DRAWINGS

[FIG. 6] Examples of the structure of immunochromatographic strips. A: Strip before use, no line observed in nitrocellulose portion. B: Strip after use, one line observed if negative (upper) and two lines observed if positive (lower). C: structure of laminated strip. D: Plastic case holding a strip.

[FIG. 7] Evaluation of sensitivity of immunochromatography for detection of F-antigen and mode of assaying. A: Assaying mode of a sample solution. B: Immunochromatography of purified F-antigen samples with various concentrations. C:

Immunochromatography of cultured pneumococcus strain (ATCC 49619) extract samples with various cell concentrations.

DETAILED DESCRIPTION OF THE INVENTION

Figure 2:
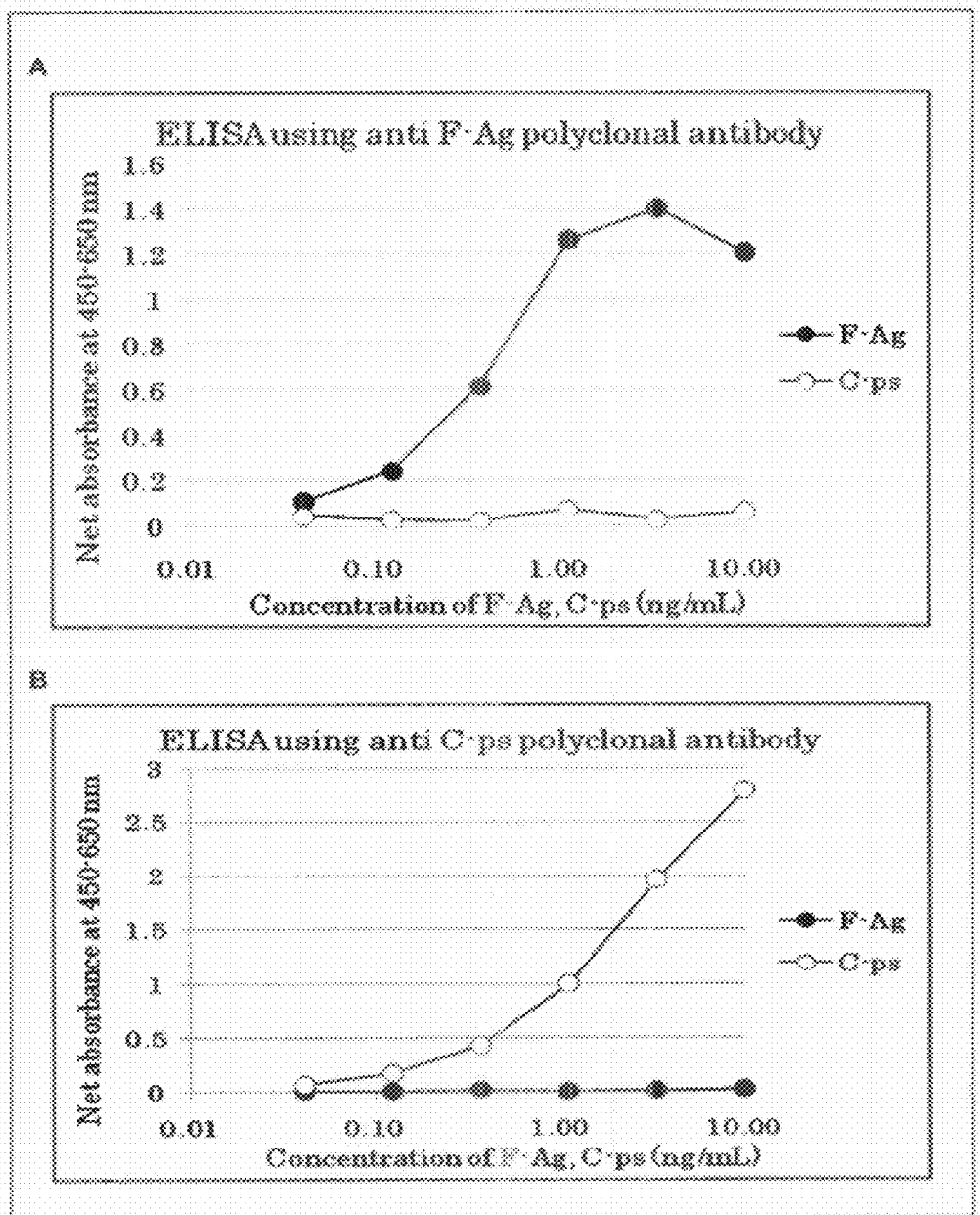
[FIG. 2] Evaluation of ELISA assay systems. A: Sandwich ELISA assay system employing an anti-F-antigen polyclonal antibody. B: Sandwich ELISA assay system employing an anti-C-ps-polyclonal antibody. F-Ag; Sample containing an F-antigen. C-ps; Sample containing a C-ps antigen.
Figure 3:
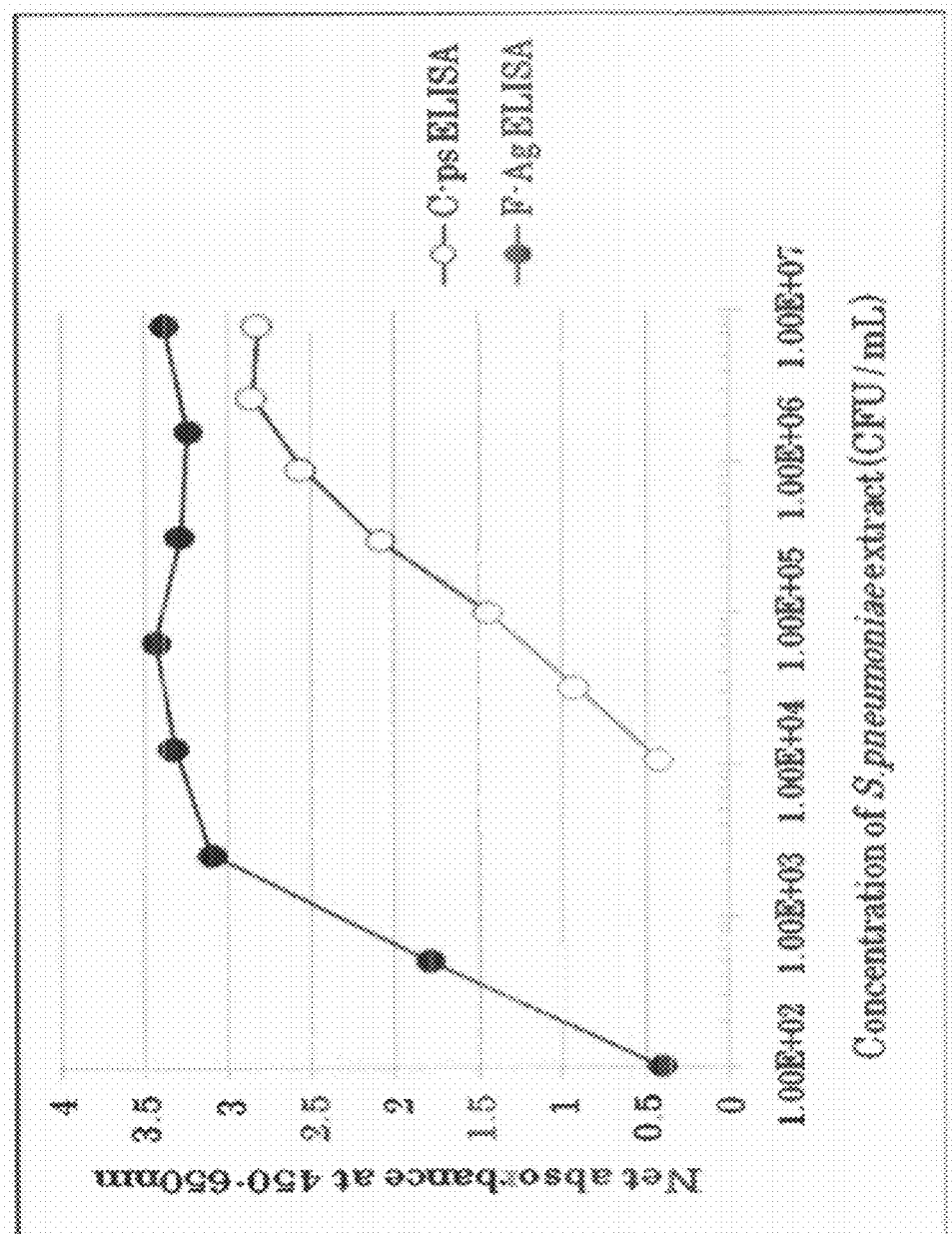
[FIG. 3] Evaluation of the Sensitivity of ELISA systems through assaying extracts of cultured pneumococcus strain (ATCC 49619). C-ps ELISA: Sandwich ELISA system employing an anti-C-ps polyclonal antibody. F-Ag ELISA: Sandwich ELISA system employing an anti-F-antigen polyclonal antibody.
Figure 4:
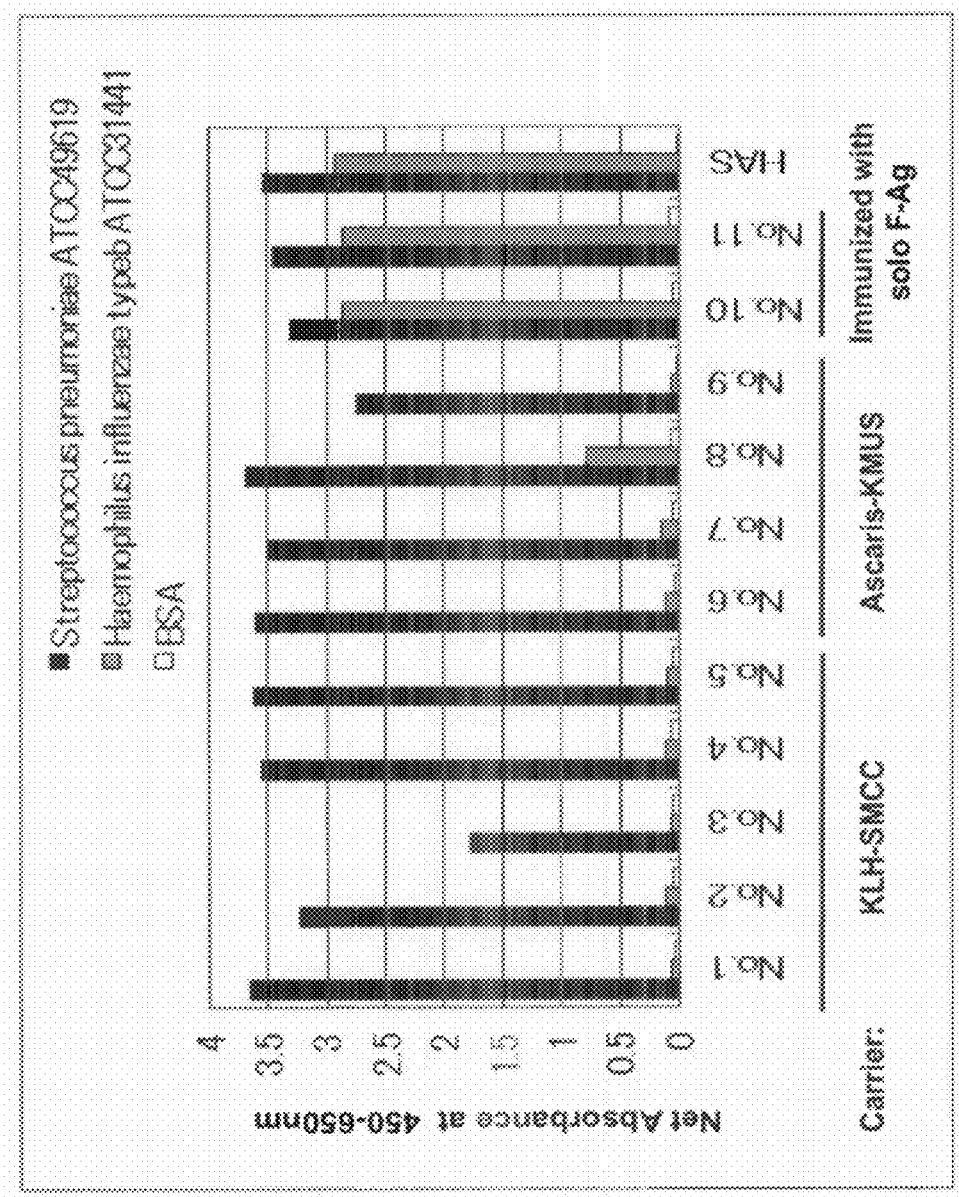
[FIG. 4] Evaluation of specificity of the antibodies of the present invention. Reaction specificity of anti-F-antigen polyclonal antibodies derived from anti-sera produced in Example 1 (Nos. 1 to 11) and known anti-phosphocholine antibody (HAS).
Figure 5:
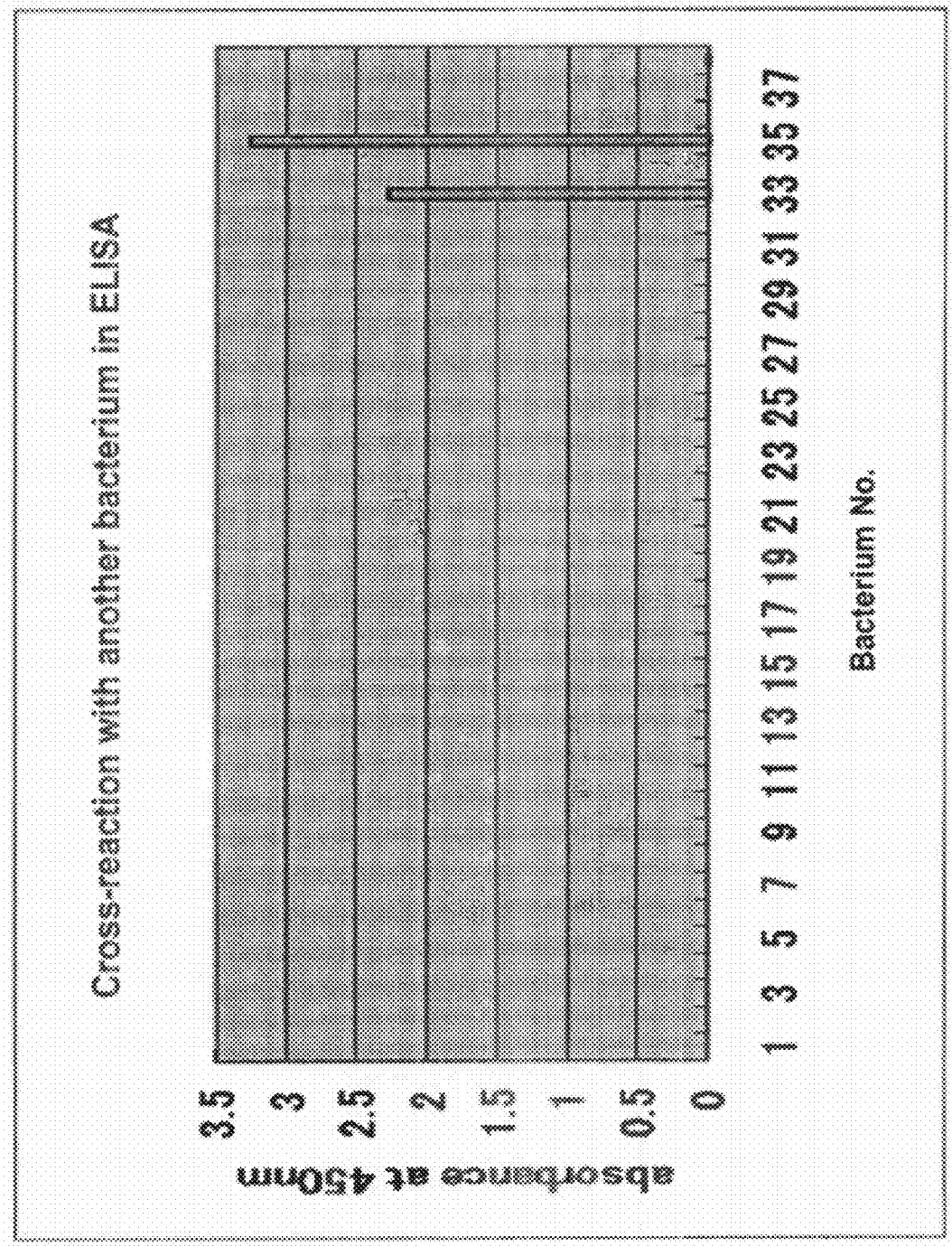
[FIG. 5] Evaluation of specificity of the ELISA system employing the antibody of the present invention. Reactivity to the bacteria listed in Table 1.

The present inventors have conceived use of the F-antigen, which has not been employed in conventional pneumococcal antigen detection kits, and have produced an anti-F-antigen antibody. Quite surprisingly, the thus-produced anti-F-antigen antibody of the present invention exhibited substantially no cross-reactivity to *Haemophilus influenzae*, to which a conventional anti-F-antigen monoclonal antibody exhibited reactivity (FIG. 4), and the ELISA system making use of the antibody exhibited substantially no cross-reactivity to a variety of bacteria including *Haemophilus influenzae* (FIG. 5). There has been reported that the F-antigen and C-ps have the same polysaccharide structure (see, for example, Sorensen, Danish Medical Bulletin 42: 47-53 (1995)). However, the anti-F-antigen antibody of the present invention exhibited substantially no reactivity to C-ps (FIG. 2). That is, the anti-F-antigen antibody of the present invention is a novel antibody which completely differs from conventional anti-F-antigen antibodies or anti-C-ps antibodies, which is highly specific to the F-antigen, and which recognizes a polysaccharide moiety. When the sensitivity of a pneumococcal antigen assay system employing the anti-F-antigen antibody of the present invention was measured, remarkably high sensitivity was observed with respect to the same sample, as compared with an assay system employing a C-ps antibody (FIG. 3).

As described hereinbelow, the anti-F-antigen antibody of the present invention may be produced through the method described in Referential Example. Specifically, an F-antigen is prepared by a known method (see, for example, Poxton et al, Biochem. J. 175: 1033-1042 (1978)). The thus-prepared F-antigen as is may be employed as an immunogen. Preferably, the prepared F-antigen is coupled with a carrier protein (e.g., the maleimide method or the pyridyl disulfide method), and the coupled F-antigen is used as an immunogen. By use of the produced immunogen, a corresponding anti-F-antigen antibody may be produced through a known method. By use of the coupled antigen as an immunogen, an anti-F-antigen antibody having no cross-reactivity to *Haemophilus influenzae* and having high specificity to pneumococcus can be produced.

No particular limitation is imposed on the carrier protein for use in the coupling reaction, so long as the protein is generally used in the art. Examples of the protein include BSA (bovine serum albumin), KLH (keyhole limpet hemocyanin), OVA (ovalbumin), and an Ascaris extract (crude extract). No particular limitation is imposed on the cross-linking agent for use in coupling of the carrier protein and the F-antigen, so long as the cross-linking agent is generally employed in coupling of proteins or peptides. A hetero divalent reaction reagent which cross-links an SH group and an amino group is preferred. Specific examples include m-maleimidobenzoyl-N-hydroxysuccinimide (MBS), N-(4-maleimidobutyryloxy) succinimide (GMBS), N-(6-maleimidocaproyloxy)succinimide (EMCS), N-(8-maleimidocapryloxy)succinimide (HMCS), N-(11-maleimidoundecanoyloxy) sduccinimide (KMUS), N-((4-(2-maleimidoethoxy)succinyl)oxy)succinimide (MESS), N-succinimidyl-4-(N-maleimidomethy-cyclohexane-1-carboxylate (SMCC), m-maleimidobenzoyl-N-hydroxysulfosuccinimide (sulfo-MBS), N-(4-maleimidobutyryloxy)sulfo-succinimide (sulfo-GMBS), N-(6-maleimidocaproyloxy) sulfosuccinimide (sulfo-EMCS), N-(8-maleimidocapryloxy) sulfosuccinimide (sulfo-HMCS), N-(11-maleimidoundecanoyloxy)sulfosuccinimide (sulfo-KMUS), and sulfosuccinimidyl-4-(N-maleimidomethyl)-cyclohexane-1-carboxylate (sulfo-SMCC).

The antibody of the present invention may be a monoclonal antibody or a polyclonal antibody, so long as the antibody gives response to an anti-F-antigen, and further encompasses an antibody having an amino acid sequence substantially identical to the above antibody. The antibody of the present invention also encompasses the corresponding antibody of the entire molecule, a recombinant antibody thereof, a fragment or modified product thereof, and a corresponding bivalent or monovalent antibody.

The monoclonal antibody may be produced through immunizing a mouse or a rat by subcutaneously, intraperitoneally, or intramuscularly injecting thereto the aforementioned immunogen or the immunogen and an additional adjuvant (e.g., Freund's adjuvant); producing hybridoma of immunocyte of the immunized animal and myeloma cells; and selecting a hybridoma that produces a specific antibody of interest among the produced hybridomas. Immunization is performed once, or several times in alternate weeks by use of an antigen in an amount, for example, 0.1 to 100 µg/body or in an absolute amount of 0.1 to 100 µg/body as reduced to the carrier protein used in coupling, preferably 1 to 10 µg/body.

The polyclonal antibody may be produced through immunizing a rabbit or a goat by subcutaneously injecting the aforementioned immunogen and an additional adjuvant (e.g., Freund's adjuvant). Immunization is performed once, or several times in alternate weeks by use of an antigen in an amount, for example, 10 to 500 µg/body or in an absolute amount of 0.1 to 1,000 µg/body as reduced to the carrier protein used in coupling, preferably 10 to 500 µg/body. Blood is sampled from the thus-immunized animal, and an IgG fraction is collected through a known method such as affinity purification (by use of Protein A or the like) or ion-exchange resin. If required, an additional purification procedure (e.g., purification through gel filtration) may be performed in combination.

The term "an antibody having a substantially identical amino acid sequence" refers to that an antibody having an amino acid sequence equivalent to that of the original antibody, except that one to a plurality of (e.g., 1 to 30, preferably 1 to 20, more preferably 1 to 10, even more preferably 1 to 5) amino acid residues are deleted, substituted, inserted, or added, and giving response to an anti-F-antigen. Techniques for deleting, substituting, inserting, or adding one to a plurality of amino acid residues in a specific amino acid sequence are known in the art. For example, a variety of methods such as site-specific mutagenesis may be employed.

So long as response to an anti-F-antigen is ensured, "the antibody having a substantially identical amino acid sequence" also encompasses an antibody having an identity in sequence of 80% or higher, preferably 85% or higher, more preferably 90% or higher, even more preferably 95% or higher, with respect to that of the original antibody. Identity between amino acid sequences is determined through, for example, the Lipman-Pearson method (Science, 227, 1435 (1985)). Specifically, homology is calculated through analysis by use of a homology analysis (search homology) program of genetic information processing software Genetyx-Win (Ver. 5.1.1) (Software Development Co., Ltd.), with ktup (unit size to compare) being set to 2.

Examples of the antibody fragment include Fab, F(ab')$_2$, Fv, Fab/c, and single-chain Fv(scFv). These antibody fragments may be produced through treating the corresponding antibody with an enzyme (e.g., papain or pepsin) or producing a gene encoding such a fragment and expressing the gene in any host cells (see, for example, Co, M. S. et al., J. Immunol. (1994) 152, 2968-2976; Better, M. & Horwitz, A. H., Methods in Enzymology (1989) 178, 476-496, Academic Press, Inc.; Plueckthun, A. & Skerra, A., Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; or Bird, R. E. et al., TIBTECH (1991) 9, 132-137).

The fragment scFv may be produced through linking the V region of the H-chain of an antibody to the V region of the L-chain thereof. In scFv, the V region of the H-chain and the V region of the L-chain are preferably linked by the mediation of a linker, preferably a peptide linker (Huston, J. S. et al., Proc. Natl. Acad. Sci. U.S.A. (1988) 85, 5879-5883). In an alternative method, a gene encoding such a linking peptide is produced, and the gene is expressed in any host cells. The modified product of the antibody may be produced through chemical modification of the antibody. The recombinant antibody may be produced by expressing any mutated antibody gene in host cells. Methods for producing recombinant antibodies and antibody modified products are known in the art.

In another aspect of the present invention, there is provided a method for detecting or quantifying a pneumococcal antigen, characterized in that the method comprises detecting or quantifying a pneumococcal F-antigen in a sample derived from a living body through immunological assay employing the anti-F-antigen antibody of the present invention. Since the detection method according to the present invention enables rapid, simple, and high-sensitivity detection of a pneumococcal antigen, rapid and correct diagnosis can be performed. Through employment of the quantification method according to the present invention, the effect and other properties of the drug to a disease caused by pneumococcus can be determined rapidly, conveniently, and with high sensitivity. Thus, these methods contribute to early stage selection of an appropriate therapeutic method.

No particular limitation is imposed on the sample derived from a living body, and examples include living-body-derived samples such as tissues, organs, and body fluids (e.g., sputum, swab of nasal cavity or epipharynx, middle ear fluid, otorrhea fluid, paranasal sinus fluid, cerebrospinal fluid, urine, blood, and lymph), and samples derived from cultured products thereof. The sample is preferably derived from sputum, swab of nasal cavity or epipharynx, middle ear fluid, otorrhea fluid, paranasal sinus fluid, cerebrospinal fluid, urine, blood, or lymph. If required, the sample is subjected to a routine preliminary treatment such as treatment with a surfactant, acid, or alkali; and extraction, concentration, dilution, etc. with heat or by other means.

The method of the present invention provides higher sensitivity as compared with conventional assay methods. Therefore, in a preferred embodiment of the present invention, samples which cannot be assayed with satisfactory sensitivity through conventional assay methods; e.g., middle ear fluid, otorrhea fluid, paranasal sinus fluid, cerebrospinal fluid, and blood-derived samples, are assayed. For example, since pneumococcus is a causal bacterium for meningitis, otitis media, sepsis, etc., the causal bacterium for these diseases can be identified with higher sensitivity by assaying middle ear fluid, otorrhea fluid, paranasal sinus fluid, cerebrospinal fluid, or a blood-derived sample through the method of the present invention.

In the method of the present invention, any immunoassay method known in the art may be employed as an immunological assay method. Examples of such methods include radioimmunoassay (RIA), enzyme immunoassay (EIA) such as ELISA, the latex agglutination method (LTIA), and immunochromatography. From the viewpoint of detection sensitivity, the sandwich assay is preferably employed. From the viewpoint of performing simple and rapid analysis, immunochromatography is preferred. When immunochromatography is employed, diagnosis of a patient on the bedside or an outpatient can be completed within a short period of time.

In the aforementioned immunological assay, any labeling substances employed in the art may be used. Examples of such labeling substances include enzymes such as horseradish peroxidase (HRP), alkaline phosphatase, and β-galactosidase; radioisotopes (RI) such as $^{125}$I, $^{32}$P, $^{14}$C, $^{35}$S, and $^{3}$H; fluorescence substances such as FITC and tetramethylrhodamine thiocyanate; luminescence substances such as chemiluminescence substances; and visualizing substances such as colloidal gold and colored latex. Alternatively, there may also be employed a sensitization system employing avidin labeled with one of the aforementioned labeling substances after primary labeling with biotin, or a detection method employing a substance having affinity to a low-molecular-weight substance such as digoxigenin and being labeled with one of the aforementioned labeling substances (e.g., antibody) after primary labeling with the low-molecular-weight substance.

The present invention also provides a kit for detecting a pneumococcal antigen, the kit employing the detection or quantitation method of the present invention. The kit of the present invention may contain an antibody which specifically recognizes a pneumococcal F-antigen. The kit of the present invention may also contain other reagents and materials for use in immunoassay. For example, the kit of the present invention, containing the antibody of the present invention, may further contain a solid phase for use in immunochromatography, ELISA, or the latex agglutination method (e.g., strip, plate, and beads), and a reagent such as a labeling substance.

EXAMPLES

The present invention will next be described in detail by way of examples, which should not be construed as limiting the invention thereto.

Referential Example 1

Preparation of Immunogen for Producing Anti-F-Antigen Antibody

1) Preparation of F-Antigen

An F-antigen was prepared according to a method by Poxton et al. (Biochem. J. 175: 1033-1042 (1978)). Firstly, pneumococcus was cultured by use a sheep blood agar medium or brain heart infusion broth, and pellets of pneumococcus were recovered through scraping or centrifugation. The thus-recovered pellets were suspended in purified water in an appropriate amount and broken through ultrasonication. This product was heated and then centrifuged, to thereby recover pellets. The procedure of suspending the pellets in purified water, ultrasonication, and centrifugation was repeated several times, to thereby sufficiently remove water-soluble components. The thus-obtained water-insoluble pellets were added to boiled SDS so as to adjust the final concentration to 2.5% SDS, and the mixture was stirred at room temperature for several hours. The procedure of centrifugation and washing with water was repeated several times, to thereby recover an insoluble component. The insoluble component was dissolved in TCA to a final concentration of 10% (TCA solution), and the solution was stirred under cooling for several hours or longer. After centrifugation, the supernatant was recovered, and TCA was removed by use of diethyl ether or the like. The product was dialyzed against purified water. The thus-obtained solution was lyophilized, to thereby yield white powder, which was thought to be a mixture of an F-antigen and nucleic acid. However, since nucleic acid has no immunogenicity, the powder obtained was employed as an antigen for producing an anti-F-antigen antibody (F-antigen) in the subsequent step.

2) Evaluation of Purity of F-Antigen

The white powder (1 mg) was weighed and dissolved in ultrapure water (1 mL), and the co-presence of protein in the solution was checked by means of a commercial protein assay kit (bicinchoninic acid method: BCA measurement kit, product of Pierce). The concentration of the protein was less than 31.25 μg/mL that was the minimum detection level of BCA measurement kit, indicating that the amount of protein co-present in the solution was extremely small.

3) Preparation of Immunogen

With reference to the report by Szu et al. (Infection and Immunity 54: 448-455 (1986)), the above-obtained F-antigen was coupled with a carrier protein (KLH: *Limulus polyphemus* hemocyanin) or a commercial Ascaris extract (produced by LSL, distributed by Cosmo Bio). Each of the carrierprotein-coupled antigen and non-coupled antigen (F-antigen) was employed as an immunogen. That is, the following procedure was performed.

1: The carrier protein suspended in phosphate buffer was treated with an SH-group reducing agent (e.g., dithiothreitol or 2-mercaptoethanol). After the treatment, the mixture was substituted by phosphate buffer through a technique such as gel filtration or dialysis.

2: In parallel to the above operation, an appropriate amount of an F-antigen was dissolved in phosphate buffer. Then, a divalent reaction reagent (sulfo-SMCC or sulfo-KMUS) which crosslinks free SH and an amino group was added to the solution, in an amount of 0.1 to 2 mg (preferably 0.2 to 1 mg) with respect to the F-antigen (1 mg).

3: The mixture was allowed to react at room temperature, and an excessive amount of the divalent reaction reagent was removed through a technique such as dialysis or gel filtration.

4: The F-antigen treated with the divalent reaction reagent in operation 2 was added in an amount of 0.1 to 10 mg (preferably 0.5 to 5 mg) to the SH-reduced carrier protein (1 mg) obtained through operation 1.

5: Reaction was performed under cooling for a sufficient period of time, and the reaction mixture was dialyzed again. The thus-recovered solution was employed as an immunogen for producing an F-antigen antibody.

Example 1

Production of Anti-F-Antigen Antibody

1) Production of Anti-F-Antigen Polyclonal Antibody

Rabbits (n=11) were immunized with the immunogen produced in Referential Example 1 through subcutaneous injection with an adjuvant (e.g., Freund's adjuvant). The amount of immunization was 10 to 500 μg/body in the case of sole use of F-antigen, and 0.1 to 1,000 μg/body, preferably 10 to 500 μg/body (absolute carrier protein amount) in the case of carrier-protein-coupled antigen. Immunization was performed once, or several times in alternate weeks. The anti-serum was partially sampled, and reactivity thereof to the antigen used in immunization was checked. Then, a large volume or the entire volume of blood was collected. In the case of large volume blood collection, collection was performed several times while immunization was continued, without imposing a load to each animal. The thus-collected whole blood was centrifuged, and the serum fraction was frozen and stored to serve as an anti-serum. An appropriate amount of the anti-serum was thawed and purified through affinity purification by use of Protein A or the like, by means of ion-exchange resin, etc., to thereby obtain an IgG fraction. In accordance with needs, purification through gel filtration was performed in combination.

2) Production of Anti-F-Antigen Monoclonal Antibody

Mice or rats were immunized with the immunogen produced in Referential Example 1 by subcutaneously, intraperitoneally, or intramuscularly injecting thereto the immunogen or the immunogen and an additional adjuvant (e.g., Freund's adjuvant). The amount of immunization was 0.1 to 100 μg/body in the case of sole use of F-antigen, and 0.1 to 100 μg/body, preferably 1 to 10 μg/body (absolute carrier protein amount) in the case of carrier-protein-coupled antigen. Immunization was performed once, or several times in alternate weeks. The anti-serum was partially sampled, and reactivity thereof to the antigen used in immunization was checked. The spleen, the thymus, and lymph nodes were removed from each animal, and immunocytes were recovered therefrom. The immunocytes were fused with mouse myeloma cells (e.g., P3U1) through a known method such as the polyethylene glycol method, to thereby produce hybridomas. From the thus-produced hybridomas, a hybridoma which reacted with the antigen of interest was selected through limiting dilution. A monoclonal antibody was purified from the ascites and the culture supernatant of the thus-selected hybridoma through affinity purification by use of Protein A or the like, by means of ion-exchange resin, etc. In accordance with needs, purification through gel filtration was performed in combination.

Example 2

Titer of Anti-F-Antigen Antibody

Figure 1:
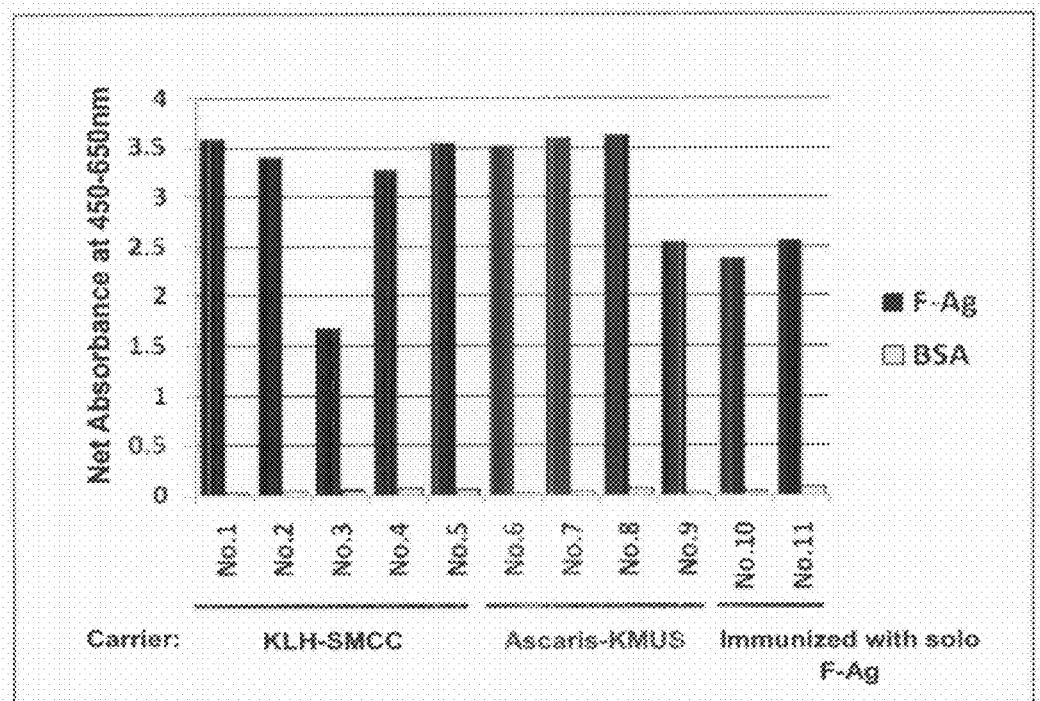
[FIG. 1] Reactivity of 10,000-fold diluted anti-sera (Nos. 1 to 11) derived from five rabbits to an F-antigen-immobilized plate (F-Ag) and to a BSA-immobilized plate (BSA).

The anti-sera, produced from 11 rabbits in Example 1 (i.e., No. 1 to No. 5: five rabbits immunized with an antigen produced from KLH as a carrier protein cross-linked with sulfo-SMCC; No. 6 to No. 9: four rabbits immunized with an antigen produced from Ascaris extract as a carrier protein cross-linked with sulfo-KMUS; and Nos. 10 and 11: two rabbits immunized with only F-antigen), were appropriately diluted (Nos. 1 to 5: ×50,000, Nos. 6 to 9: ×50,000, and Nos. 10 and 11: ×1,000). The titer of each anti-serum was evaluated by reacting the anti-serum with an F-antigen immobilized plate. FIG. 1 shows the results. As is clear from FIG. 1, all the anti-sera obtained from the 11 rabbits were found to strongly react with the F-antigen immobilized plate. These anti-sera were also found to not react with a bovine serum albumin (BSA) immobilized plate serving as a control. Thus, all the sera produced through the aforementioned method were found to exhibit intense anti-F-antigen responsivity.

Example 3

Antigen Reactivity in Sandwich ELISA Employing Anti-F-Antigen Antibody

IgG fractions were obtained from the anti-sera of No. 1 and 5 among anti-sera of Example 1 through Protein A purification and gel filtration purification. By use of these polyclonal antibodies, sandwich ELISA assay systems were established, and performance thereof was evaluated. In other words, each of the samples containing the F-antigen or C-ps (0.041 to 10 ng/mL) was added to an immobilized plate on which a purified antibody derived from the No. 5 serum had been fixed, to thereby react the antigen with the antibody. In the assay system employing the anti-F-antigen antibody, the plate was washed, and a biotin-labeled purified antibody derived from the No. 1 serum was added thereto, to thereby react the sample with the plate. The plate was washed again, and horse radish peroxidase (HRP) labeled streptoavidin was added to the plate to thereby react the streptoavidin with biotin. Subsequently, color development of HRP was measured by means of an absorbance meter. In a similar manner, a sandwich ELISA assay system employing an anti-C-ps polyclonal antibody was produced by use of commercial C-ps, and color development of HRP was measured.

On the basis of the obtained absorbance data, the two assay systems were compared with each other. Hitherto, it has been reported that the F-antigen and C-ps have the same polysaccharide structure (Sorensen, Danish Medical Bulletin 42: 47-53 (1995)). Thus, both assay systems were thought to cross-react with C-ps and F-antigen. However, as shown in FIG. 2, the sandwich ELISA assay system employing the anti-F-antigen polyclonal antibody of the present invention detected the F-antigen but did not detect C-ps (FIG. 2A).

Similarly, the sandwich ELISA assay system employing the C-ps detected C-ps but did not detect the F-antigen (FIG. 2B).

Thus, the anti-F-antigen antibody of the present invention was found to specifically recognize only F-antigen. The anti-F-antigen antibody of the present invention did not cross-react with C-ps (FIG. 2), indicating that the antibody is a completely novel one differing from conventionally employed anti-C-ps antibodies.

Example 4

Bacterium Reactivity in Sandwich ELISA Employing Anti-F-Antigen Antibody

The reactivity of the two sandwich ELISA assay systems produced in Example 3 to a pneumococcus cell extract was investigated. The cell extract was a solution produced through breaking pneumococcus (ATCC 49619) obtained through culturing, by means of a surfactant, ultrasonication, or other means. As shown in FIG. 3, the assay system employing the anti-F-antigen antibody of the present invention was able to detect a pneumococcal antigen in the pneumococcus cell extract with a sensitivity 100 times that obtained by the assay system employing the anti-C-ps antibody. Accordingly, the ELISA system employing the anti-F-antigen antibody of the present invention was found to detect pneumococcus in a sample derived from a living body with remarkably high sensitivity, as compared with a conventionally employed C-ps assay systems. Notably, as shown in FIG. 2, when the purified antigen was assayed, the sensitivity was almost the same (about 0.1 ng/mL) in both assay systems. Therefore, the difference in sensitivity observed in assaying living body-derived samples was suggested to be conceivably attributed to the difference in expression amount between the antigens in pneumococcus.

Example 5

Crossreactivity of Sandwich ELISA System Employing Anti-F-Antigen Antibody to Other Bacterial Species Known anti-F-antigen antibodies and F-antigen detection systems (Kolberg et al., Microbial Pathogenesis 22: 321-329 (1997) or Stuertz et al., J. Clin. Microbiol. 36: 2346-2348 (1998)) employ a phosphorylcholine moiety as an epitope. Therefore, these antibodies and detection systems are suggested to disadvantageously have strong cross-reactivity to C-ps, *Haemophilus influenzae*, etc. other than F-antigen.

Thus, sandwich ELISA assay systems employing each of the anti-F-antigen polyclonal antibodies of the present invention derived from the anti-sera (Nos. 1 to 11) produced in Example 1 were investigated in terms of cross-reactivity among bacteria. For comparison, a similar experiment was performed by use of a mouse monoclonal antibody HAS employing a phosphorylcholine moiety as an epitope (Statens Serum Institut, Denmark, Reference: Infection and Immunity 1984; 43: 876-878, Microbial Pathogenesis 1993; 14: 299-305).

1) Cross-Reactivity Between Pneumococcus and *Haemophilus Influenzae*

Cultured cells of pneumococcus (ATCC 49619) and those of *Haemophilus influenzae*(Type B, ATCC 31441) were broken through ultrasonication. Each bacterial extract was subjected to protein assay by means of a commercial protein assay kit (bicinchoninic acid method: BCA assay kit, Pierce). The extract of each bacterium was diluted with D-PBS to a concentration of 1.0 µg/mL, and the solution was immobilized overnight on an ELISA plate. The plate was blocked through a conventional technique, and each of appropriately diluted anti-sera produced in Example 1 (Nos. 1 to 5: ×50,000, Nos. 6 to 9: ×50,000, and Nos. 10 and 11: ×1,000) or a diluted liquid of the aforementioned HAS antibody (×125) was caused to react with the plate. Subsequently, each plate was color-developed with an HRP-labeled anti-rabbit IgG antibody or an HRP-labeled anti-mouse IgM antibody, and color development of HRP was measured by means of an absorbance meter. As a control plate, a BSA-immobilized plate was employed. FIG. 4 shows the results.

The anti-sera of Nos. 10 and 11 obtained through immunization with only F-antigen, and the HAS antibody employing phosphocholine as an epitope reacted both with the pneumococcus-broken antigen and the *Haemophilus influenzae*-broken antigen. In contrast, the anti-sera of Nos. 1 to 9, produced through immunization with a coupled antigen, exhibited no cross-reactivity to *Haemophilus influenzae*, indicating high specificity to pneumococcus, although only the anti-serum No. 8 exhibited weak cross-reactivity. Therefore, antibodies produced from an antigen prepared by cross-linking the F-antigen to a carrier protein as an immunogen, which antibodies have no cross-reactivity to *Haemophilus influenzae*, which the HAS antibody has, are suggested to be anti-F-antigen antibodies not recognizing phosphocholine. In contrast, anti-sera produced from the F-antigen not coupled with a carrier protein serving as an immunogen were found to contain an antibody having phosphorylcholine as an epitope, which is similar to the HAS antibody.

2) Comparison of Cross-Reactivity Among a Plurality of Bacteria Species

Cross-reactivity was further investigated among many bacteria species. The procedure of Example 5-1) was repeated, except that the bacteria listed in Table 1 were used, to thereby assess the reactivity of the antibody of the present invention. FIG. 5 shows the results. The antibody of the present invention exhibited cross-reactivity to *S. mitis*, similar to the case of the antibody produced by Stuertz et al. (Stuertz et al., J. Clin. Microbiol. 36: 2346-2348 (1998)), but exhibited no reactivity to other bacteria.

TABLE 1

|    | ATCC No. | Bacteria | Bacterial concentration in extract (CFU/mL) |
|----|----------|----------|---------------------------------------------|
| 1  | 25285    | *Bacteroides fragilis* | 1.1E+07 |
| 2  | BAA-589  | *Bordetella pertussis* | 9.5E+07 |
| 3  | 66396    | *Candida albicans* | 6.0E+06 |
| 4  | 10700    | *Corynebacterium pseudodiphtheriticum* | 5.0E+07 |
| 5  | 14116    | *Cryptococcus neoformants* | 4.3E+05 |
| 6  | 8486     | *Eubacterium limosum* | 1.3E+07 |
| 7  | 9006     | *Haemophilus influenzae*, a | 2.7E+06 |
| 8  | 10211    | *Haemophilus influenzae*, b | 5.0E+06 |
| 9  | 9007     | *Haemophilus influenzae*, c | 3.9E+06 |
| 10 | 9008     | *Haemophilus influenzae*, d | 5.0E+06 |
| 11 | 8142     | *Haemophilus influenzae*, e | 4.5E+06 |
| 12 | 700222   | *Haemophilus influenzae*, f | 3.4E+06 |
| 13 | 7901     | *Haemophilus parainfluenzae* | 5.5E+07 |
| 14 | 9997     | *Klebsilla pneumoniae* | 3.6E+07 |
| 15 | 33152    | *Legionella pneumophila* | 3.6E+07 |
| 16 | 33153    | *Legionella pneumophila* | 9.5E+07 |
| 17 | 33216    | *Legionella pneumophila* | 1.0E+07 |
| 18 | 33270    | *Micromonus micros* | 4.1E+07 |
| 19 | 8193     | *Moraxella catarrhalis* | 5.0E+06 |
| 20 | 6250     | *Neisseria meningitidis* | 1.6E+07 |
| 21 | 15032    | *Prebotella intermedia* | 5.5E+07 |
| 22 | 25845    | *Prebotella melaninogenica* | 5.0E+07 |

TABLE 1-continued

| ATCC No. | Bacteria | Bacterial concentration in extract (CFU/mL) |
|---|---|---|
| 23 | 9027 | *Pseudomonas aeruginosa* | 5.5E+07 |
| 24 | 700699 | *Staphylococcus aureus* | 2.7E+07 |
| 25 | 14776 | *Staphylococcus aureus* | 5.5E+07 |
| 26 | 33397 | *Streptococcus anginosus* (group G) | 3.3E+07 |
| 27 | 12386 | *Streptococcus agalactiae* (group B) | 4.1E+07 |
| 28 | 27513 | *Streptococcus constellaus* | 3.3E+07 |
| 29 | 27823 | *Streptococcus constellaus* | 1.2E+06 |
| 30 | 9528 | *Streptococcus equi* (group C) | 5.0E+06 |
| 31 | 9895 | *Streptococcus intermedius* | 7.0E+07 |
| 32 | 27335 | *Streptococcus intermedius* | 3.2E+07 |
| 33 | 49456 | *Streptococcus mitis* | 1.2E+07 |
| 34 | 35037 | *Streptococcus oralis* (group A) | 7.0E+05 |
| 35 | 49619 | *Streptococcus pneuminiae* | 1.2E+07 |
| 36 | 10556 | *Streptococcus sanguis* | 6.0E+07 |
| 37 | 9963 | *Streptococcus* sp. (group F) | 4.4E+07 |
| 38 | 8149 | *Haemophilus influenzae*, nontype | 1.1E+07 |

The anti-F-antigen antibody of the present invention which antibody recognizes a polysaccharide moiety exhibited high specificity to pneumococcus, as compared with conventional anti-F-antigen antibodies employing phosphorylcholine as an epitope. Furthermore, since the anti-F-antigen antibody of the present invention has no reactivity to *Haemophilus influenzae*, which readily causes mixed infection with pneumococcus in clinical settings, the antibody of the invention is useful in clinical tests without being interfered by *Haemophilus influenzae*. In addition, the ELISA assay system employing the antibody of the present invention exhibited a sensitivity of 0.041 to 10 ng/mL (shown in Example 3), which is remarkably higher (about 75 times) as compared with conventionally reported sensitivities of ELISA assay systems (e.g., 3.1 to 50 ng/mL, reported by the aforementioned Stuertz et al.).

Referential Example 2

Immunochromatography Means

In the present invention, immunochromatography may be performed through a conventional technique. For example, chromatographic means including strips and other materials as shown in FIG. 6 may be employed. One embodiment of the chromatographic means has, on one side of the substrate such as a plastic base sheet at one end, a sample application portion (sample pad) and a portion holding a labeled anti-F-antigen antibody in a dry state (conjugate pad), a nitrocellulose portion, and a portion for absorbing an excessive amount of the sample (absorption pad). In the case where the labeled anti-F-antigen antibody solution and a sample are absorbed by the sample pad, the conjugate pad may be omitted. The sample pad, conjugate pad and absorption pad are preferably formed of glass fiber, cellulose, cotton, or a porous material formed from a mixture thereof (e.g., filtration paper). Nitrocellulose having a pore size of 1.0 to 20 µm (preferably 5.0 to 15.0 µm) is preferred.

Onto the nitrocellulose portion, the aforementioned purified anti-F-antigen polyclonal antibody (concentration: 0.1 to 10 mg/mL, preferably 0.2 to 5 mg/mL) is applied (see the test line). Onto the area apart from the test line, for example, a goat or mouse IgG having anti-rabbit IgG activity (concentration: 0.1 to 10 mg/mL) is applied (see the control line). After drying, the chromatographic means is blocked by protein, polymer, etc. Examples of the blocking material which may be used in the invention include proteins such as skimmed milk, BSA, casein, and gelatin; and polymers such as polyvinyl alcohol (PVA), polyvinylpyrrolidone (PVP), and polyethylene glycol (PEG).

The antibody labeling material is preferably colloidal gold having a particle size of 20 to 150 nm (preferably 30 to 100 nm). Alternatively, colored latex particles and other colloidal metals may also be employed. These labeling materials are bound to an antibody through direct adsorption thereof onto colloid or latex particles, covalent binding via another protein, covalent binding via functional groups on latex particles, or other appropriate method. Similar to the case of nitrocellulose, the labeling material may be blocked by use of proteins such as skimmed milk, BSA, casein, and gelatin; and polymers such as polyvinyl alcohol (PVA), polyvinylpyrrolidone (PVP), and polyethylene glycol (PEG). Then, the aforementioned porous material is impregnated with the labeled anti-F-antigen polyclonal antibody produced through the aforementioned method and a protein such as skimmed milk, BSA, casein, or gelatin, or a polymer such as PVA, PVP, or PEG, and a saccharide and dried, to thereby provide a conjugate pad. The conjugate pad, a sample pad, an absorption pad, and the nitrocellulose portion formed through the above method are stacked on the substrate, to thereby fabricate an immunochromatographic strip. The strip can be used, when it is built in a plastic case or a laminate seal is attached thereto (FIGS. 6C and 6D).

Example 6

Evaluation of Performance of Sandwich Immunochromatography Employing Anti-F-Antigen Antibody An immunochromatographic strip having a conjugate pad in which a colloidal gold-labeled anti-F-antigen antibody has been harbored in a dry state was fabricated. A sample such as exudate, swab, sputum, blood, cerebrospinal fluid, or urine originating from otitis media, pneumonia, meningitis, etc. was diluted with a surfactant-containing phosphate buffer or the like. A chromatographic strip was dipped in the diluted sample (sample extract), to thereby develop the sample (FIG. 7A). Fifteen minutes after start of development, whether the sample is positive or negative was visually checked. As a result, a red line was observed at the test line position when the F-antigen concentration fell within a range of 10 to 0.6 ng/mL, whereby the sample was confirmed to be positive. In contrast, in the case where a buffer was used instead of the F-antigen, no red line was observed at the test line position, whereby the sample was confirmed to be negative (FIG. 7B). Through the same technique, a bacterium extract having a known cell concentration was assayed by means of the same immunochromatographic strip. When the only buffer was applied (cell concentration: 0), no line was observed at the test line position, which was similar to the above case. In contrast, when a pneumococcus extract was applied, the test line was able to be confirmed to a cell concentration of $10^3$ CFU/mL, indicating that the sample was positive (FIG. 7C).

The invention claimed is:

1. An isolated antibody which specifically binds to a pneumococcal F-antigen and wherein said antibody exhibits substantially no cross-reactivity to a *Haemophilus influenzae* type b or a pneumococcal C-ps antigen, wherein said antibody is prepared by coupling the F-antigen to keyhole limpet hemocyanin (KLH) or Ascaris extract by a cross-linking agent and raising said antibody against the coupled F-antigen.

2. A method for detecting or quantitating a pneumococcal antigen, comprising detecting or quantitating a pneumococcal F-antigen in a sample derived from a living body through immunological assay employing an antibody as recited in claim 1.

3. A method according to claim 2, wherein the sample derived from a living body is derived from the middle ear or the paranasal sinus.

4. A kit for detecting a pneumococcal antigen, the kit containing an antibody as recited in claim 1.

5. A method for detecting or quantitating a pneumococcal antigen, comprising detecting or quantitating a pneumococcal F-antigen in a sample derived from a living body through immunological assay employing a kit according to claim 4.

6. The antibody of claim 1, wherein said antibody is a monocolonal antibody.

7. The antibody of claim 1, wherein said antibody is a polycolonal antibody.

8. The antibody of claim 1, wherein said F-antigen is coupled to keyhole limpet hemocyanin (KLH).

9. The antibody of claim 1, wherein said F-antigen is coupled to an Ascaris extract.

10. The antibody of claim 9, wherein the Ascaris extract is a crude extract.

11. The antibody of claim 1, wherein said cross-linking agent is selected from the group consisting of m-maleimidobenzoyl-N-hydroxysuccinimide (MBS), N-(4-maleimidobutyryloxy)succinimide (GMBS), N-(6-maleimidocaproyloxy)succinimide (EMCS), N-(8-maleimidocapryloxy)succinimide (HMCS), N-(11-maleimidoundecanoyloxy)succinimide (KMUS), N-((4-(2-maleimidoethoxy)succinyl)oxy)succinimide (MESS), N-succinimidyl-4-(N-maleimidomethyl)-cyclohexane-1-carboxylate (SMCC), m-maleimidobenzoyl-N-hydroxysulfosuccinimide (sulfo-MBS), N-(4-maleimidobutyryloxy)sulfosuccinimide (sulfo-GMBS), N-(6-maleimidocaproyloxy)sulfosuccinimide (sulfo-EMCS), N-(8-maleimidocapryloxy)sulfosuccinimide (sulfo-HMCS), N-(11-maleimidoundecanoyloxy)sulfosuccinimide (sulfo-KMUS), and sulfosuccinimidyl-4-(N-maleimidomethyl)-cyclohexane-1-carboxylate (sulfo-SMCC).

* * * * *